US008802860B2

(12) United States Patent
Krüger et al.

(10) Patent No.: US 8,802,860 B2
(45) Date of Patent: Aug. 12, 2014

(54) METHOD FOR PRODUCING SUBSTITUTED PYRIDIN-2-ONE

(75) Inventors: Joachim Krüger, Düsseldorf (DE); Danja Großbach, Wuppertal (DE); Holger Paulsen, Hilden (DE); Walter Kroh, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/643,244

(22) PCT Filed: Apr. 26, 2011

(86) PCT No.: PCT/EP2011/056588
§ 371 (c)(1),
(2), (4) Date: Dec. 21, 2012

(87) PCT Pub. No.: WO2011/134963
PCT Pub. Date: Nov. 3, 2011

(65) Prior Publication Data
US 2013/0116443 A1 May 9, 2013

(30) Foreign Application Priority Data
Apr. 29, 2010 (DE) .......................... 10 2010 028 362

(51) Int. Cl.
C07D 213/78 (2006.01)
A61K 31/44 (2006.01)
(52) U.S. Cl.
USPC .......................................... 546/300; 514/345
(58) Field of Classification Search
None
See application file for complete search history.

(56) References Cited

U.S. PATENT DOCUMENTS

| 7,049,443 | B2 | 5/2006 | Hester, Jr. |
| 7,157,456 | B2 | 1/2007 | Straub et al. |
| 7,265,140 | B2 | 9/2007 | Josyula et al. |
| 7,351,823 | B2 | 4/2008 | Berwe et al. |
| 7,576,111 | B2 | 8/2009 | Straub et al. |
| 7,585,860 | B2 | 9/2009 | Straub et al. |
| 7,592,339 | B2 | 9/2009 | Straub et al. |
| 7,767,702 | B2 | 8/2010 | Straub et al. |
| 8,153,670 | B2 | 4/2012 | Zhu et al. |
| 8,198,267 | B2 | 6/2012 | Allerheiligen et al. |
| 2006/0069260 | A1 | 3/2006 | Zhang et al. |
| 2007/0026065 | A1 | 2/2007 | Benke et al. |
| 2008/0026057 | A1 | 1/2008 | Benke |
| 2008/0306070 | A1 | 12/2008 | Perzborn et al. |
| 2010/0029651 | A1 | 2/2010 | Härter et al. |
| 2010/0184740 | A1 | 7/2010 | Allerheiligen et al. |
| 2010/0261759 | A1 | 10/2010 | Allerheiligen et al. |
| 2010/0292230 | A1 | 11/2010 | Lerchen et al. |

OTHER PUBLICATIONS

Yip, S Org Lett 2007 vol. 9 pp. 3469-3472.*
Bundgaard:"Design of Prodrugs: Bioreversible Derivatives for Various Functional Groups and Chemical Entities," Elsevier Science Publishers B.V., 1985, pp. 1-92.
Gould, et al.:"Inhibitors of Blood Coagulation Factors Xa and IIa Synergize to Reduce Thrombus Weight and Thrombin Generation in Vivo and in Vitro," Journal of Thrombosis and Haemostasis, 2006, 4(4):834-841.
Hauptman, et al.:"Synthetic Inhibitors of Thrombin and Factor Xa: From Bench to Bedside," Thrombosis Research, 1999, 93: 203-241.
Kahns, et al.:"N-Acyl Derivatives as Prodrug Forms for Amides: Chemical Stability and Enzymatic Hydrolysis of Various N-acyl and N-alkoxycarbonyl Amide Derivatives," International Journal of Pharmaceuticals, 1991, 71:31-43.
Kerns, et al.:"Drug-like Properties: Concepts, Stucture Design and Methods: from ADME to Toxicity Optimization," 2008, Academic Press, pp. 70 & 73.
Quan, et al.:"The Race to an Orally Active Factor Xa Inhibitor: Recent Advances," Current Opinion in Drug Discovery & Development, 2004, 7(4): 460-469.
Reuf, et al.:"New Antithrombotic Drugs on the Horizon," Expert Opin. Investig. Drugs, 2003, 12(5): 781-797.
Roehrig, et al.:"Discovery of the Novel Antithrombotic Agent 5-Chloro-N-({(5S)-2-oxo-3-[4-(3-oxomorpholin-4-yl) phenyl]-1,3-oxazolidin-5-yl}methyl)thiophene- 2-carboxamide (BAY 59/7939): An Oral, Direct Factor Xa Inhibitor," J. Med. Chem., 2005, 48(19):5900-5908.
Sohn, et al.:"Current Status of the Anticoagulant Hirudin: Its Boitechnological Production and Clinical Practice," Aook. Microbiol. Biotechnol., 2001, 57:606-613.
Walenga, et al.:"Factor Xa Inhibitors: Today and Beyond," Current Opinion in Investigational Drugs, 2003, 4(3): 278-281.
Xie, et al.:"Anti-AIDS Agents. 52.† Synthesis and Anti-HIV Activity of Hydroxymethyl (3′R,4′R)-3′,4′-Di-O-(S)-camphanoyl-(+)-cis-khellactone Derivatives," J. Med. Chem., 2004, 47:756-760.
Orjiekwee, et al.: "Synthesis and Characterization of New Picolinate Metal Complexes," Synthesis and Reactivity in Inorganic, Metal Organic, and Nano-Metal Chemistry, 2005, 35:695-702.
Yip, et al: "Room-Temperature_Copper-Catalyzed_α-Arylation of Malonates," Organic Letters, 2007, 9(17):3469-3472.

* cited by examiner

*Primary Examiner* — Heidi Reese
(74) *Attorney, Agent, or Firm* — Karen B. King

(57) ABSTRACT

The present invention relates to a process for the preparation of substituted 3-(2-hydroxyethyl)-1-[4-nitrophenyl]pyridin-2(1H)-ones which serve as important intermediate compounds for producing drugs.

17 Claims, No Drawings

METHOD FOR PRODUCING SUBSTITUTED PYRIDIN-2-ONE

The present invention relates to a process for the preparation of substituted 3-(2-hydroxyethyl)-1-[4-nitrophenyl]pyridin-2(1H)-ones which serve as important intermediate compounds for producing drugs.

The compound 5-chloro-N-{[(5S)-3-{4-[3-{2-[(trans-4-hydroxycyclohexyl)amino]ethyl}-2-oxopyridin-1(2H)-yl]-3,5-dimethylphenyl}-2-oxo-1,3-oxazolidin-5-yl]methyl}thiophene-2-carboxamide is known from WO 2008/155032 and corresponds to the Formula (Ia)

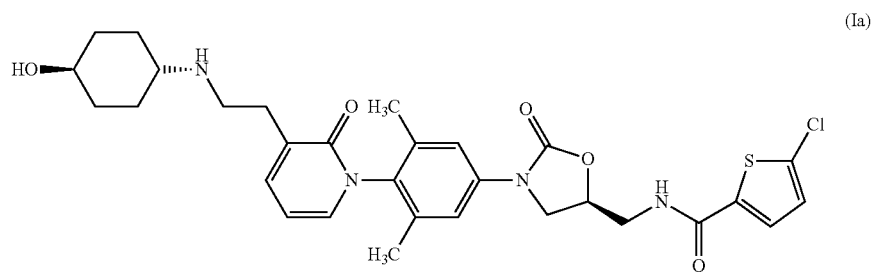

(Ia)

and the compound 5-chloro-N-[((5S)-3-{4-[3-(2-hydroxyethyl)-2-oxopyridin-1(2H)-yl]-3-methylphenyl}-2-oxo-1,3-oxazolidin-5-yl)methyl]thiophene-2-carboxamide is known from WO 2008/155033 and corresponds to the Formula (IIb)

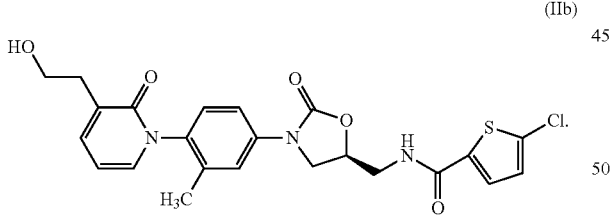

(IIb)

The compounds of the Formula (Ia) and (IIb) are dual inhibitors of the blood clotting factors Xa and thrombin (factor IIa) which act in particular as anticoagulants. The compounds inhibit both thrombin and also factor Xa and, by inhibiting thrombin production and activity on clots, prevent their potential growth.

WO 2008/155032 also describes a method for preparing the compounds of the Formula (Ia) and (IIb):

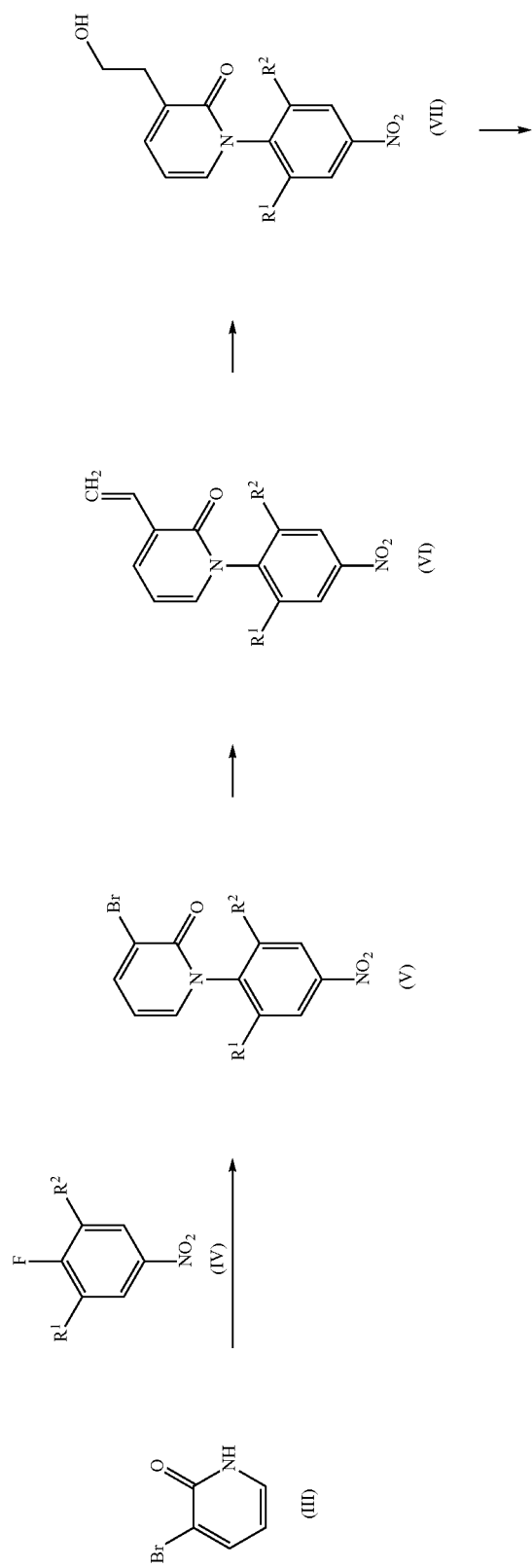

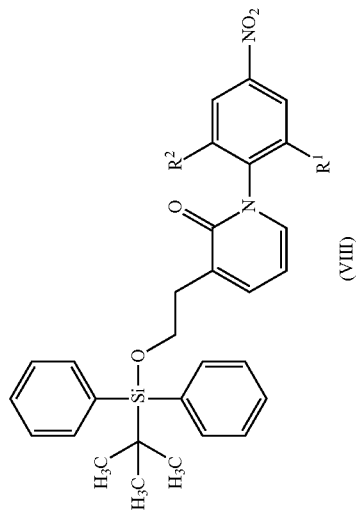
-continued
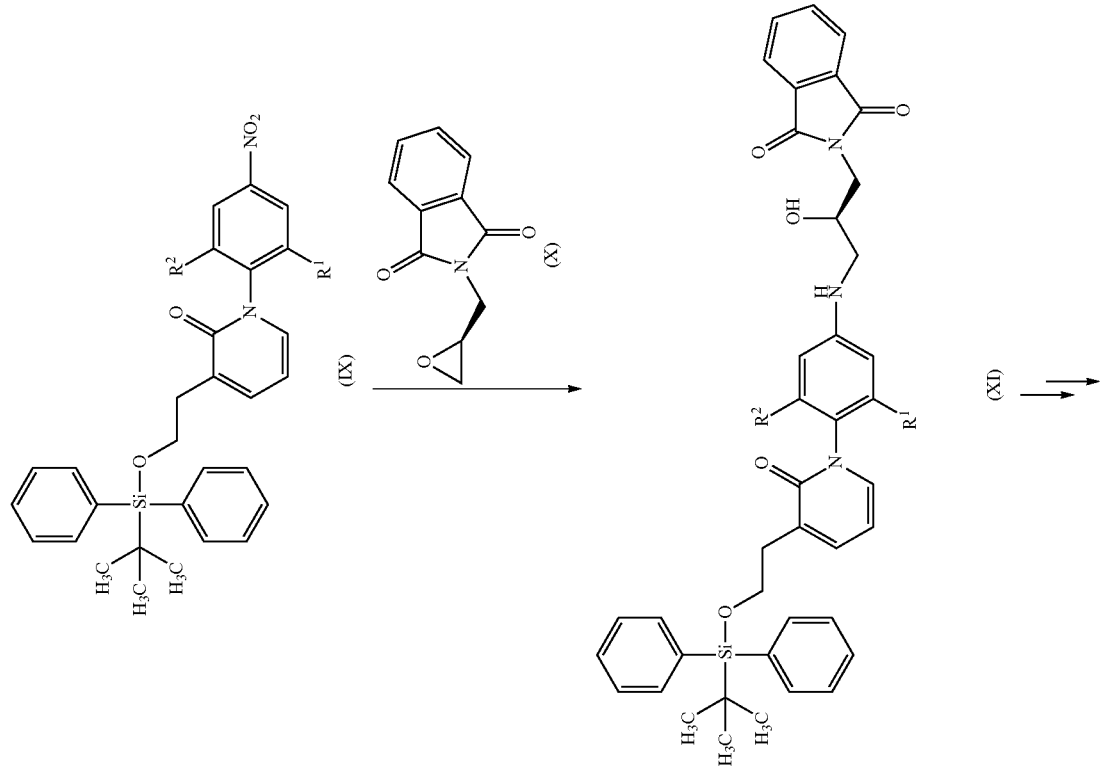

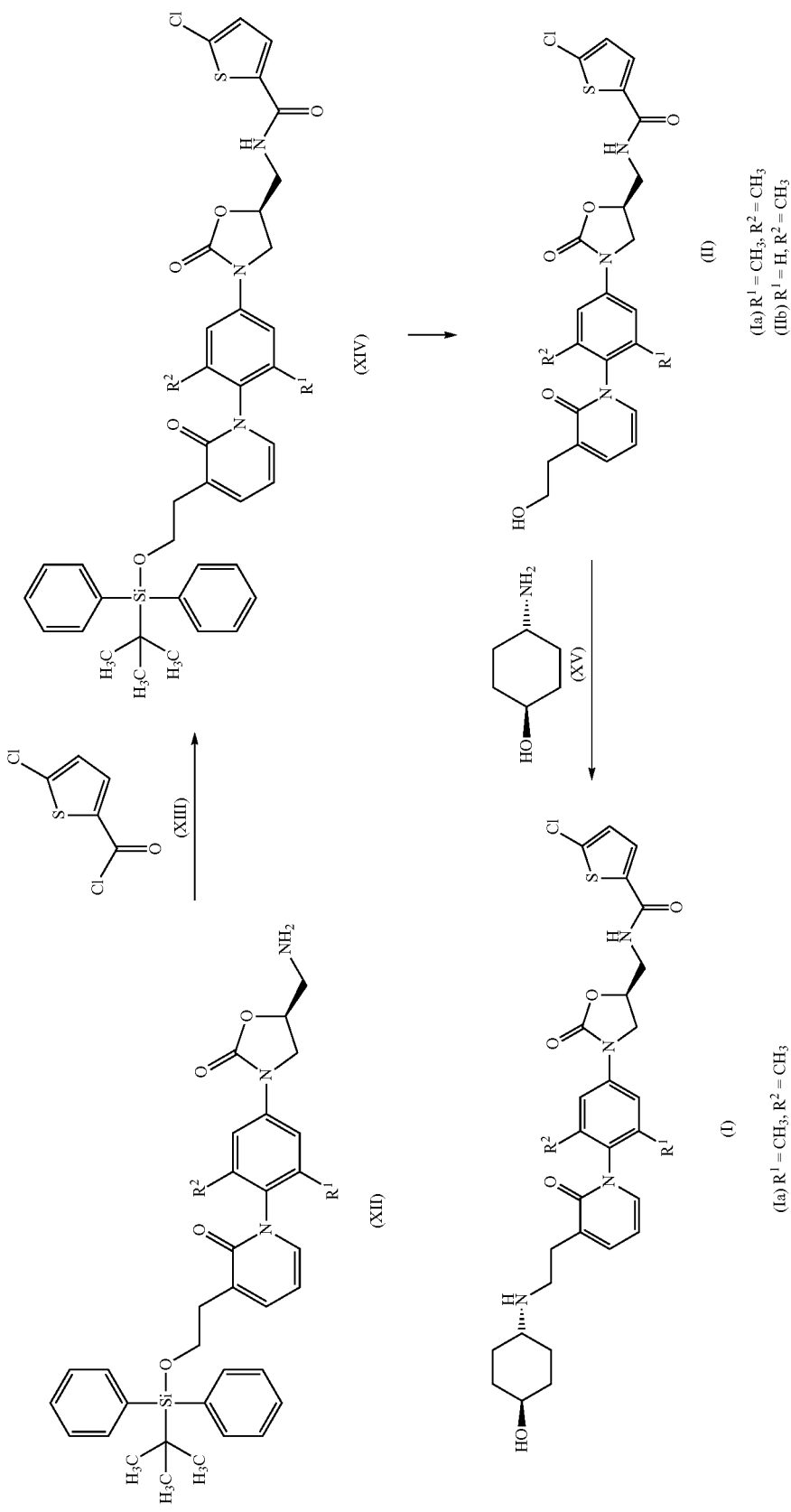

To prepare the compound of the Formula (Ia), 3-bromopy-ridin-2(1H)-one (III) is reacted with 1-fluoro-2,5-dimethyl-4-nitrobenzene (IV) to give 3-bromo-1-(2,6-dimethyl-4-nitrophenyl)pyridin-2(1H)-one (V). Then, (V) is converted with tributylvinyl tin and tetrakis(triphenylphosphine)palladium into 1-(2,6-dimethyl-4-nitrophenyl)-3-vinylpyridin-2(1H)-one (VI). Hydroboration and oxidation of (VI) produces 1-(2,6-dimethyl-4-nitrophenyl)-3-(2-hydroxyethyl)pyridin-2(1H)-one (VII). In order to protect the hydroxy group, (VII) is reacted with tert-butyl(chloro)diphenylsilane in the presence of a base, giving 3-(2-{[tert-butyl(diphenyl)silyl]oxy}ethyl)-1-(2,6-dimethyl-4-nitrophenyl)pyridin-2(1H)-one (VIII). The reduction of the nitro group in (VIII) leads to 1-(4-amino-2,6-dimethylphenyl)-3-(2-{[tert-butyl(diphenyl)silyl]oxy}ethyl)pyridin-2(1H)-one (IX). Then follows the reaction of (IX) with (S)-epoxyphthalimide (X) to give 2-[(2R)-3-({4-[3-(2-{[tert-butyl(diphenyl)silyl]oxy}ethyl)-2-oxopyridin-1(2H)-yl]-3,5-dimethylphenyl}amino)-2-hydroxypropyl]-1H-isoindole-1,3(2H)-dione (XI). Ring closure to the oxazolidinone and cleaving off the phthalimide group produces starting from (XI) 1-{4-[(5S)-5-(aminomethyl)-2-oxo-1,3-oxazolidin-3-yl]-2,6-dimethylphenyl}-3-(2-{[tert-butyl-(diphenyl)silyl]oxy}ethyl)pyridin-2(1H)-one (XII), which is reacted with 5-chlorothiophene-2-carbonyl chloride (XIII) to give N-[((5S)-3-{4-[3-(2-{[tert-butyl-(diphenyl)silyl]oxy}ethyl)-2-oxopyridin-1(2H)-yl]-3,5-dimethylphenyl}-2-oxo-1,3-oxazolidin-5-yl)methyl]-5-chlorothiophene-2-carboxamide (XIV). Cleaving off the protective group in (XIV) produces 5-chloro-N-[((5S)-3-{4-[3-(2-hydroxyethyl)-2-oxopyridin-1(2H)-yl]-3,5-dimethylphenyl}-2-oxo-1,3-oxazolidin-5-yl)methyl]thiophene-2-carboxamide (IIa), which is reacted with trans-4-aminohexanol (XV) to give 5-chloro-N-{[(5S)-3-{4-[3-{2-[(trans-4-hydroxycyclohexyl)amino]ethyl}-2-oxopyridin-1(2H)-yl]-3,5-dimethylphenyl}-2-oxo-1,3-oxazolidin-5-yl]methyl}thiophene-2-carboxamide (Ia).

However, this process known from WO 2008/155032 has various disadvantages in the implementation of the reaction, which have a particularly unfavourable effect when preparing the compound of the Formula (I) and (II) on an industrial scale. The synthesis described in WO 2008/155032 has proven to be particularly disadvantageous in the synthesis steps (V) to (VI) (Stille coupling) and (VI) to (VII) (hydroboration).

Thus, implementation on an industrial scale permits no toxic reagents. This is per se disadvantageous; moreover, these toxic substances have to be removed from the end product (I) and/or (II) to below the maximum limit permissible in each case in the product for regulatory reasons, which signifies additional expenditure. Furthermore, the reagents should be easy and cost-effective to obtain.

Arising from this, the object of the present invention is to provide a simplified process for the preparation of the compounds of the Formulae (I or Ia) and (II or IIb) on an industrial scale while avoiding toxic reagents.

Kwong et al., Org. Lett., 2007, 9, 3469-3472 describes the reaction of iodoaromatics and diethyl malonate with copper iodide in the presence of 2-pyridinecarboxylic acid and caesium carbonate at room temperature in dioxane. Caesium carbonate is used by Kwong et al. in an excess of 3.0 equivalents and, as well as contributing to a high cost, also contributes significantly to the salt content.

Surprisingly, it has now been found that by modifying certain reaction parameters during the synthesis known from WO 2008/155032, it is possible to prepare the compounds of the Formulae (I or Ia) and (II or IIb) also in larger amounts in good yield and purity. For this, the Stille coupling in synthesis step (V) to (VI) was replaced by a copper-catalyzed malonic acid ester addition, saponification and decarboxylation, and the hydroboration in synthesis step (VI) to (VII) is carried out by means of a simple reduction with borane complex. These synthesis steps permit an efficient scale-up of the synthesis, during which, consequently, more cost-effective, readily available and less toxic reagents are used.

The present invention provides a process for the preparation of compounds of the Formula

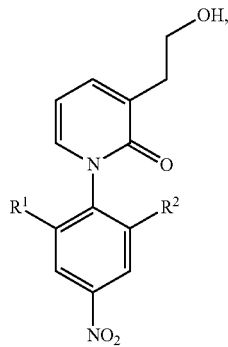

(VII)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl,
characterized in that the carboxyl group in compounds of the Formula

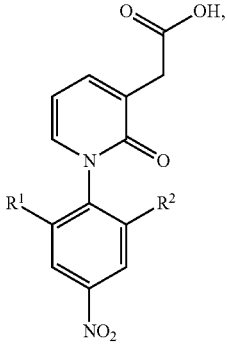

(XVI)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl,
is reduced in the presence of a borane complex.

Preference is given to a process for the preparation of compounds of the Formula (VII), in which $R^1$ is hydrogen or methyl and $R^2$ is methyl, or $R^1$ is hydrogen and $R^2$ is methoxy or methoxymethyl, characterized in that the carboxyl group in compounds of the Formula (XVI), in which $R^1$ is hydrogen or methyl and $R^2$ is methyl, or $R^1$ is hydrogen and $R^2$ is methoxy or methoxymethyl, is reduced in the presence of a borane complex.

Very particular preference is given to the process for the preparation of compounds of the Formula (VII), in which $R^1$ is methyl and $R^2$ is methyl, characterized in that the carboxyl group in compounds of the Formula (XVI), in which $R^1$ is methyl and $R^2$ is methyl, is reduced in the presence of a borane complex.

The reduction of the carboxyl group in the presence of a borane complex takes place in a solvent, preferably in a temperature range from 0° C. up to the reflux of the solvent at atmospheric pressure.

Solvents are, for example, ethers such as dioxane, tetrahydrofuran, 2-methyltetrahydrofuran, 1,2-dimethoxyethane or methyl tert-butyl ether, or other solvents such as dichloromethane or toluene, preferably 2-methyltetrahydrofuran.

Borane complexes are, for example, borane-dimethyl sulphide, borane-tetrahydrofuran, borane diethylaniline or catecholborane, preferably borane diethylaniline.

The borane complex is used in excess, preference being given to using 1 to 5 equivalents of borane complex, particularly preferably 2 equivalents of borane complex.

In one preferred embodiment of the present invention, the reaction temperature is 0° C. to 50° C., the reaction temperature particularly preferably 15° C. to 25° C.

When carrying out the process according to the invention, the diethylaniline is preferably separated off from the aqueous phase rendered acidic by hydrochloric acid by means of extraction after sodium chloride has been added. The extraction takes place preferably with ethyl acetate, dichloromethane or toluene.

In this way, the hydroboration used in WO 2008/155032 and WO 2008/155033 can be avoided. Hydroborations are generally carried out in high dilution and the reagents are expensive. The subsequent oxidation step is complex on an industrial scale since high safety standards have to be observed.

The present invention also provides a process for the preparation of compounds of the Formula

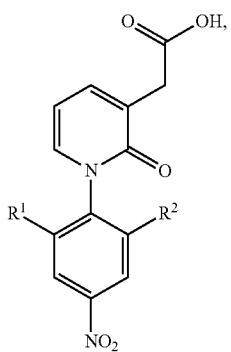

(XVI)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl, characterized in that compounds of the Formula

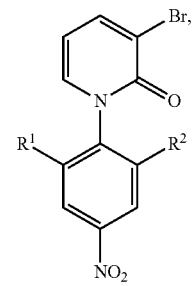

(V)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl, are reacted in a one-pot process firstly in the presence of a copper catalyst with a malonic acid ester and a base and then with a base and water.

Preference is given to a process for the preparation of compounds of the Formula (XVI) in which $R^1$ is hydrogen or methyl and $R^2$ is methyl, or $R^1$ is hydrogen and $R^2$ is methoxy or methoxymethyl, characterized in that compounds of the Formula (V) in which $R^1$ is hydrogen or methyl and $R^2$ is methyl, or $R^1$ is hydrogen and $R^2$ is methoxy or methoxymethyl, are reacted in a one-pot process firstly in the presence of a copper catalyst with a malonic acid ester and then with a base.

Very particular preference is given to a process for the preparation of compounds of the Formula (XVI) in which $R^1$ is methyl and $R^2$ is methyl, characterized in that compounds of the Formula (V) in which $R^1$ is methyl and $R^2$ is methyl are reacted in a one-pot process firstly in the presence of a copper catalyst with a malonic acid ester and then with a base.

The first step of the reaction with a malonic acid ester in the presence of a copper catalyst and a base takes place in a solvent, preferably in a temperature range from 15° C. up to the reflux of the solvent at atmospheric pressure.

Solvents are, for example, dioxane, tetrahydrofuran and 2-methyltetrahydrofuran, preferably dioxane.

Copper catalysts are for example a bis(2-pyridinecarboxylato)copper(II) complex produced beforehand or its various hydrate forms, or copper catalysts produced in-situ from copper iodide, copper chloride, copper(II) bromide, copper(II) triflate or copper(II) sulphate with 2-pyridinecarboxylic acid, preference being given to bis(2-pyridinecarboxylato)copper (II) complex produced beforehand.

Malonic acid esters are, for example, diethylmalonic acid esters, dibenzylmalonic acid esters, di-tert-butylmalonic acid esters or potassium ethylmalonic acid esters, preferably diethylmalonic acid esters.

Bases are, for example, sodium or potassium tert-butylate, potassium, sodium or caesium carbonate, caesium fluoride or sodium hydride, preferably sodium or potassium tert-butylate, particularly preferably sodium tert-butylate.

In a preferred embodiment of the present invention, the malonic acid ester is deprotonated in an upstream step with the base and then the compound of the Formula (V) and the catalyst are added to the reaction mixture.

In a preferred embodiment of the present invention, the malonic acid ester is added dropwise to a suspension of potassium tert-butylate in dioxane at a temperature of from 80° C. to 100° C., preferably a temperature of 90° C., in the step upstream of the deprotonation.

In a preferred embodiment of the present invention, when using potassium tert-butylate as base, the compound of the Formula (V) is used in a concentration of from 0.1 to 0.4 molar, preferably a concentration of from 0.15 to 0.3 molar.

In a preferred embodiment of the present invention, when using sodium tert-butylate as base, the compound of the Formula (V) is used in a concentration of from 0.2 to 0.6 molar, preferably a concentration of from 0.25 to 0.4 molar.

In a preferred embodiment of the present invention, the copper catalyst is prepared separately and added to the reaction as copper complex. For this purpose, copper(II) chloride is reacted with 2-pyridinecarboxylic acid in an acetone/ethanol mixture and with the addition of a 0.1% strength urea solution (*Synthesis and Reactivity in Inorganic, Metal-Organic, and Nano-Metal Chemistry*, 35(9), 695-702; 2005). The desired copper complex (bis(2-pyridinecarboxylato)copper(II) complex) is produced quantitatively and in crystalline form from the reaction mixture and is filtered off with suction under nitrogen and washed with acetone.

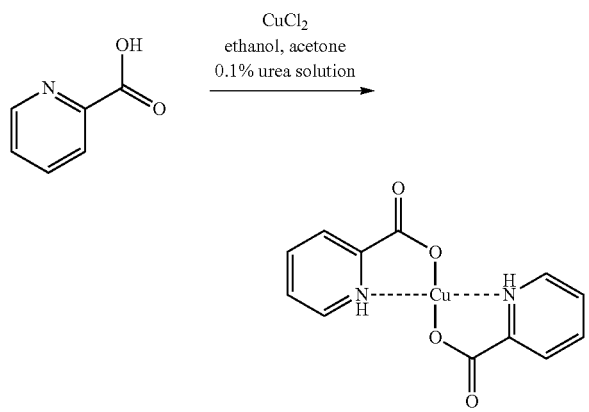

Surprisingly in the case of the preparation of [1-(2-methyl-4-nitrophenyl)-2-oxo-1,2-dihydropyridin-3-yl]acetic acid, it was established that this bis(2-pyridinecarboxylato)copper(II) complex produced beforehand is more active, by several orders of magnitude, than the in-situ produced catalyst of copper iodide and 2-pyridinecarboxylic acid. For example, in a potassium tert-butylate-mediated process with in-situ production of the catalyst, 20 mol % of copper iodide and 40 mol % of 2-pyridinecarboxylic acid are required so that the starting compound reacts completely to give the product within 8 h. By contrast, if the same batch is run with 10 mol % of the separately produced bis(2-pyridinecarboxylato)copper(II) complex, then the reaction is complete after 4 h under otherwise identical conditions. This effect proves to be even more drastic in the case of the sodium tert-butylate-mediated reactions. The use of 20 mol % of copper iodide and 40 mol % of 2-pyridinecarboxylic acid for the in-situ preparation of the catalyst leads to a conversion of only 48% after 8 hours whereas 7.5 mol % of the bis(2-pyridinecarboxylato)copper(II) complex produces a conversion of 99% over the course of 3.5 h.

In one preferred embodiment of the present invention, 3.0 to 4.0 equivalents of diethylmalonic acid ester are used, preferably 3.5 equivalents of diethylmalonic acid ester.

The advantage of this process over the process described by Kwong et al., *Org. Lett.*, 2007, 9, 3469-3472 is that the copper catalyst is prepared separately and added to the reaction mixture in crystalline form. The reaction with this catalyst proceeds much more rapidly and with a smaller amount of catalyst. Moreover, it is possible to dispense with caesium carbonate, which is expensive and brings with it a large salt content.

The second step after reaction with a base takes place in a solvent in combination with water, preferably in a temperature range from 15° C. to 40° C. at atmospheric pressure.

Solvents are, for example, dioxane/water or tetrahydrofuran/water, preferably dioxane/water.

Bases are, for example, alkali metal hydroxides such as lithium, sodium or potassium hydroxide, preferably sodium hydroxide.

In a preferred embodiment of the present invention, the resulting reaction mixture is concentrated after the copper-catalyzed reaction with a malonic acid ester in the first stage and the insoluble constituents are filtered off before the reaction mixture is reacted in the second stage with a base.

In a preferred embodiment of the present invention, the purification of the compound of the Formula (XVI) takes place by washing the aqueous solution of the sodium salt of the dimalonic acid formed as intermediate, the subsequent acidification of the aqueous solution, in order to permit decarboxylation, and the extraction of the compound of the Formula (XVI) from the aqueous solution with methylene chloride.

In a preferred embodiment of the present invention, the resulting crude product of the compound of the Formula (XVI) is recrystallized in a subsequent step for further purification from a mixture of dioxane and methyl tert-butyl ether.

The preparation of the compounds of the Formulae (I) to (V) and (VIII) to (XV) takes place as already also disclosed in WO 2008/155032 and WO 2008/155033.

The reaction of compounds of the Formula (V) to compounds of the Formula (XVI) can also take place in two stages so that firstly compounds of the Formula (V) are reacted in the presence of a copper catalyst with a malonic acid ester and a base and the reaction mixture is reacted and worked-up to give compounds of the Formula

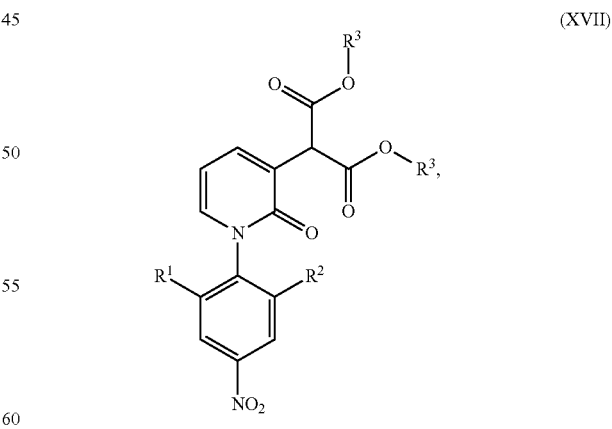

(XVII)

in which
R$^1$ is hydrogen or C$_1$-C$_3$-alkyl
and
R$^2$ is C$_1$-C$_3$-alkyl,
or
R$^1$ is hydrogen and
$R^2$ is $C_1$-$C_3$-alkoxy or $C_1$-$C_3$-alkoxymethyl,
and
$R^3$ is ethyl, tert-butyl or benzyl,
and, in the second stage, compounds of the Formula (XVII) are reacted with a base and water to give compounds of the Formula (XVI).

The reaction in the first stage takes place like the reaction of the first step of the one-pot process and the reaction in the second stage takes place like the reaction in the second step of the one-pot process.

Synthesis scheme:

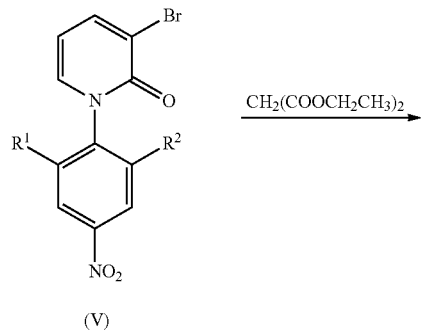

(V)

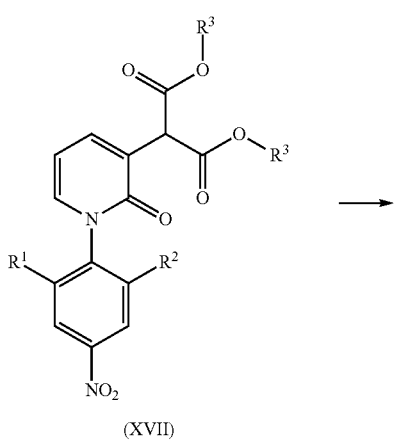

(XVII)

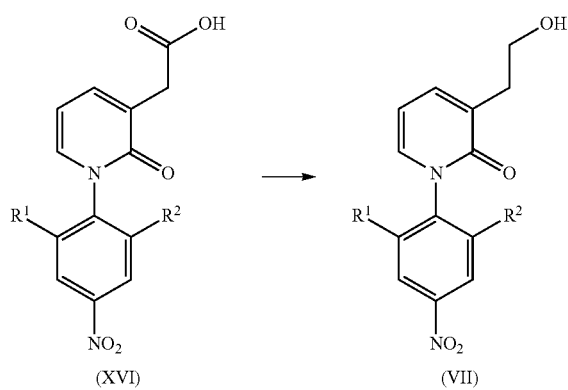

(XVI)          (VII)

The present invention provides compounds of the Formula

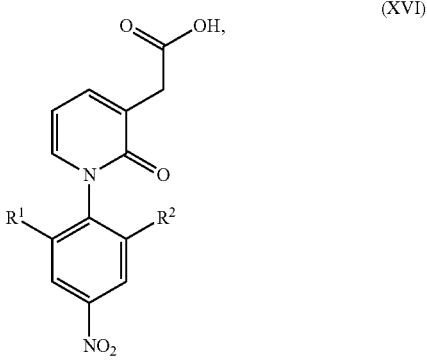

(XVI)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl,
and their salts, their solvates and the solvates of their salts.

The present invention also provides compounds of the Formula (XVI) in which $R^1$ is hydrogen or methyl and $R^2$ is methyl, or $R^1$ is hydrogen and $R^2$ is methoxy or methoxymethyl.

The present invention also provides compounds of the Formula (XVI) in which $R^1$ is methyl and $R^2$ is methyl.

Compounds according to the invention are the compounds of the Formula (XVI) and their salts, solvates and solvates of the salts; the compounds encompassed by Formula (XVI) of the formulae specified below and their salts, solvates and solvates of the salts, and also the compounds encompassed by Formula (XVI) and specified below as working examples, and their salts, solvates and solvates of the salts provided the compounds encompassed by Formula (XVI) and specified below are not already salts, solvates and solvates of the salts.

The compounds according to the invention can exist in stereoisomeric forms (enantiomers, diastereomers) depending on their structure. The invention therefore encompasses the enantiomers or diastereomers and their respective mixtures. The stereoisomerically uniform constituents can be isolated in a known manner from such mixtures of enantiomers and/or diastereomers.

If the compounds according to the invention can exist in tautomeric forms, the present invention encompasses all tautomeric forms.

Within the context of the present invention, preferred salts are physiologically acceptable salts of the compounds according to the invention. Also encompassed, however, are salts which are themselves not suitable for pharmaceutical applications but can be used, for example, for isolating or purifying the compounds according to the invention.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethansulphonic acid, toluenesulphonic acid, benzenesulphonic acid, naphthalene-disulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases such as for example and preferably alkali metal salts (e.g. sodium and potassium salts), alkaline earth metal salts (e.g. calcium and magnesium salts) and ammonium salts, derived from ammonia or organic amines having 1 to 16 carbon atoms, such as for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Within the context of the invention, solvates is the term used to refer to those forms of the compounds according to the invention which, in solid or liquid state, form a complex as a result of coordination with solvent molecules. Hydrates are a specific form of solvates in which the coordination takes place with water.

The invention is illustrated in more detail below by means of preferred working examples, to which, however, it is not limited. Unless stated otherwise, all quantitative data refer to percentages by weight.

EXAMPLES

| Abbreviations | |
|---|---|
| CDI | carbonyldiimidazole |
| d | doublet (in NMR) |
| TLC | thin layer chromatography |
| DCI | direct chemical ionization (in MS) |
| dd | double doublet (in NMR) |
| DMAP | 4-dimethylaminopyridine |
| DMF | N,N-dimethylformamide |
| DMSO | dimethyl sulphoxide |
| d | day(s) |
| of Th. | of theory (for yield) |
| eq. | equivalent(s) |
| ESI | electrospray ionization (in MS) |
| h | hour(s) |
| HPLC | high-pressure, high-performance liquid chromatography |
| LC-MS | liquid chromatography-coupled mass spectroscopy |
| m | multiplet (in NMR) |
| min | minute(s) |
| MS | mass spectroscopy |
| NMP | N-methylpyrrolidone |
| NMR | nuclear magnetic resonance spectroscopy |
| RP | reverse phase (in HPLC) |
| RT | room temperature |
| $R_t$ | retention time (in HPLC) |
| s | singlet (in NMR) |
| THF | tetrahydrofuran |

NMR spectroscopy: all spectra were calibrated against tetramethylsilane as internal standard ($\delta=0$).
HPLC, LC-MS and GC-MS Methods:
Method 1 (HPLC): column Zorbax SB-Aq 3 mm×150 mm, 3.5 μm; temperature: 45° C.; eluent A: aqueous buffer consisting of 1.36 g/l potassium dihydrogen phosphate and 1.15 g/l phosphoric acid (85% strength); eluent B: acetonitrile; gradient: 0-20 min 95% A to 20% A, 20-25 min 20% A; flow: 0.5 ml/min; UV detection at 210 nM.
Method 2 (HPLC): column Zorbax SB-Aq 3 mm×150 mm, 3.5 μm; temperature: 45° C.; eluent A: aqueous buffer consisting of 1.36 g/l potassium dihydrogen phosphate and 0.68 ml phosphoric acid (85% strength)/l water; eluent B: acetonitrile; gradient: 0-3 min 80% A to 45% A, 3-13 min 45% A to 20% A, 13-25 min 20% A; flow: 0.5 ml/min; UV detection at 220 nM.

Method 3 (HPLC): instrument: HP 1100 with DAD detection; column: Kromasil 100 RP-18, 60 mm×2.1 mm, 3.5 μm; eluent A: 5 ml perchloric acid (70% strength)/l water, eluent B: acetonitrile; gradient: 0 min 2% B, 0.5 min 2% B, 4.5 min 90% B, 6.5 min 90% B, 6.7 min 2% B, 7.5 min 2% B; flow: 0.75 ml/min; temperature: 30° C.; UV detection at 210 nm.

Method 4 (LC-MS): instrument: Waters ACQUITY SQD UPLC System; column: Waters Acquity UPLC HSS T3 1.8 μ 50 mm×1 mm; eluent A: 1 l water+0.25 ml 99% strength formic acid, eluent B: 1 l acetonitrile+0.25 ml 99% strength formic acid; gradient: 0.0 min 90% A→1.2 min 5% A→2.0 min 5% A; furnace: 50° C.; flow: 0.40 ml/min; UV detection: 210-400 nm.

Method 5 (LC-MS): instrument: Micromass Quattro Premier with Waters UPLC Acquity; column: Thermo Hypersil GOLD 1.9 μ 50 mm×1 mm; eluent A: 1 l water+0.5 ml 50% strength formic acid, eluent B: 1 l acetonitrile+0.5 ml 50% strength formic acid; gradient: 0.0 min 90% A→0.1 min 90% A→1.5 min 10% A→2.2 min 10% A; furnace: 50° C.; flow: 0.33 ml/min; UV detection: 210 nm.

Method 6 (LC-MS): MS instrument type: Micromass ZQ; HPLC instrument type: HP 1100 Series; UV DAD; column: Phenomenex Gemini 3 μ 30 mm×3.00 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow: 0.0 min 1 ml/min, 2.5 min/3.0 min/4.5 min 2 ml/min; furnace: 50° C.; UV detection: 210 nm.

Method 7 (GC-MS): instrument: Micromass GCT, GC6890; column: Restek RTX-35, 15 m×200 μm×0.33 m; constant flow with helium: 0.88 ml/min; furnace: 70° C.; inlet: 250° C.; gradient: 70° C., 30° C./min→310° C. (hold for 3 min).

Example 1

Preparation of 3-bromopyridone

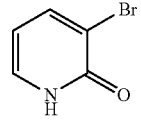

Over the course of 2 hours at 35-40° C., 2.69 kg (16.8 mol) of bromine were metered into a solution of 5.0 kg (42.0 mol) of potassium bromide and 1.60 kg (16.8 mol) of 2-hydroxypyridine. The mixture was stirred for 1 h at 35° C. and then cooled to 22° C. The pH was adjusted to pH 9.5 with a 23% strength sodium hydroxide solution and the product was isolated via a suction filter. Washing was carried out twice with in each case 2 l of water and twice with in each case 1 l of 1:1 water/methanol. The product was dried to constant weight in vacuo at 40° C. This gave 1.53 kg (52%) of the desired product.

HPLC (method 1): $R_t$=13.9 min with 97 area %.

$^1$H NMR (500 MHz, DMSO-$d_6$): δ [ppm]=6.14 (t, 1H), 7.46 (dd, 1H), 7.92 (dd, 1H), 11.95-12.29 (m, 1H).

MS (TOF EI$^+$): 173

Example 2

Preparation of 3-bromo-1-(2-methyl-4-nitrophenyl)pyridin-2(1H)-one

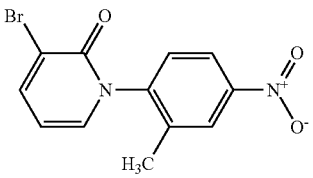

A suspension of 125 g (718 mmol) of 3-bromopyridone, 106 g (682 mmol) of 2-fluoro-5-nitrotoluene and 183 g (862 mmol) of anhydrous tripotassium phosphate in 325 ml of NMP was heated at 120° C. for 4 h. At 90° C., 1250 ml of water were added and the mixture was cooled to 20° C. with stirring. After-stirring was carried out for 16 h, followed by isolation via a suction filter. Washing was carried out twice with in each case 500 ml of water and twice in each case with 500 ml of 1:1 water/methanol. Finally, in vacuo at 40° C., drying to constant weight was carried out. This gave 178 g (80%) of the desired product. The purity of the product can be increased further to ≥99 area % by recrystallization e.g. from dioxane or acetonitrile.

HPLC (method 1): $R_t$=13.9 min with 97 area %.

$^1$H NMR (500 MHz, DMSO-$d_6$): δ [ppm]=2.17 (s, 3H), 6.37 (t, 1H), 7.65 (d, 1H), 7.69 (dd, 1H), 8.10 (dd, 1H), 8.21 (dd, 1H), 8.34 (d, 1H).

MS (DCI-NH$_3$): [M+H]$^+$ 309

Example 3

Preparation of [1-(2-methyl-4-nitrophenyl)-2-oxo-1,2-dihydropyridin-3-yl]acetic acid

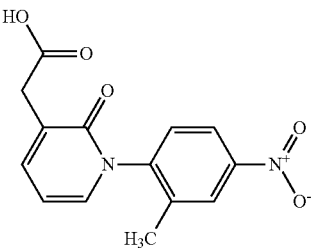

Over the course of 15 min, 180 g of diethyl malonate were added dropwise to a solution of 110 g (1.14 mmol) of sodium tert-butylate in 700 ml of dioxane. The mixture was diluted with 200 ml of dioxane and after-stirred for 1 h at 20° C. 7.5 g (24 mmol) of bis(2-pyridinecarboxylato)copper(II) complex and 100 g (0.32 mol) of 3-bromo-1-(2-methyl-4-nitrophenyl)pyridin-2(1H)-one were added and the mixture was heated to 95° C. Over the course of 3.5 h, ca. 300 ml of dioxane were distilled off, the mixture was cooled to 20° C. and 900 ml of water were added. The mixture was admixed with 108 ml of concentrated sodium hydroxide solution and stirred for 1 h at 45° C. At 20° C., 800 ml of dichloromethane were added and the mixture was filtered over kieselguhr. The organic phase was discarded, and the water phase was admixed with 1 l of dichloromethane and adjusted to pH 1 with 37% strength hydrochloric acid. Stirring was carried out for 2 h until the gas stopped evolving. The water phase was extracted with 240 ml of dichloromethane and the combined organic phases were concentrated to ca. 250 ml. The mixture was admixed with 400 ml of dioxane and concentrated again to ca. 250 ml. This process step was repeated. 500 ml of methyl tert-butyl ether were added and the mixture was stirred for 1 h at 0-5° C. Filtration via a suction filter, washing twice with in each case 100 ml of methyl tert-butyl ether and drying in vacuo to constant weight were carried out. This gave 74.3 g (80%) of the desired carboxylic acid.

HPLC (method 1): $R_t$=10.3 min with 99 area %.

$^1$H NMR (400 MHz, DMSO-$d_6$): δ [ppm]=2.14 (s, 3H), 3.43 (s, 2H), 6.38 (t, 1H), 7.52 (t, 1H), 7.57 (d, 1H), 8.19 (dd, 1H), 8.31 (d, 1H).

MS (DCI-NH$_3$): [M+H]$^+$ 289.

Example 4

Preparation of 3-(2-hydroxyethyl)-1-(2-methyl-4-nitrophenyl)pyridin-2(1H)-one

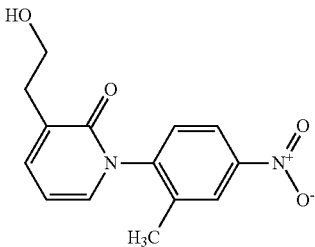 [SMILES: Cc1cc([N+](=O)[O-])ccc1-n1cccc(CCO)c1=O]

At 20° C., over the course of 20 min, 56.8 g (348 mmol) of borane-dimethylaniline complex were added dropwise to a solution of 50 g (174 mmol) of [1-(2-methyl-4-nitrophenyl)-2-oxo-1,2-dihydropyridin-3-yl]acetic acid in 100 ml of 2-methyl-THF. The mixture was after-stirred for 16 h and diluted with 500 ml of dichloromethane. Over the course of 30 min, this mixture was metered into a solution of 50 g of sodium chloride in 500 ml of 1M hydrochloric acid. The mixture was after-stirred for 1 h and the organic phase was washed again with 500 ml of a solution of 50 g of sodium chloride in 500 ml of 1M hydrochloric acid. Washing with 500 ml of a saturated aqueous sodium hydrogen carbonate solution, drying over sodium sulphate and evaporation were carried out. 40 g (84%) of the desired alcohol were obtained.

HPLC (method 1): $R_t$=11.2 min with 100 area %.

$^1$H NMR (400 MHz, CDCl$_3$): δ [ppm]=2.27 (s, 3H), 2.89 (t, 2H), 3.89 (t, 2H), 6.34 (t, 4H), 7.11 (dd, 1H), 7.41 (d, 1H), 8.20 (dd, 1H), 8.25 (d, 1H).

MS (DCI-NH$_3$): [M+H]$^+$ 275.

Example 5

Preparation of 3-bromo-1-(2-methoxy-4-nitrophenyl)pyridin-2(1H)-one

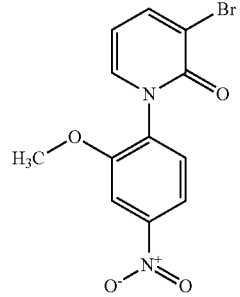

36.2 g of 3-bromopyridone (87% purity, 0.18 mol) and 29.4 g of 4-fluoro-3-methoxynitrobenzene (0.17 mol) were introduced as initial charge in 180 ml of N-methylpyrrolidone; 46.1 g of anhydrous potassium phosphate (0.22 mol) were added and the reaction mixture was carried out at 120° C. for 6 h. After cooling to 90° C., water was added and the mixture was cooled to room temperature. The precipitate was filtered off, washed with water and stirred with a methanol/water mixture (1:1). The solid was filtered off, washed and dried in the air. This gave 38.7 g (66%) of the desired target compound.

HPLC (method 3): $R_t$=3.50 min.
LC-MS (method 4): $R_t$=0.84 min.
$^1$H NMR (400 MHz, DMSO-$d_6$): δ [ppm]=3.91 (s, 3H), 6.30 (t, 1H), 7.64 (dd, 1H), 7.70 (d, 1H), 7.96 (dd, 1H), 8.00 (m, 1H), 8.04 (dd, 1H).
MS (ES+): [M+H]$^+$ 327 or 325.

Example 6

Preparation of diethyl [1-(2-methoxy-4-nitrophenyl)-2-oxo-1,2-dihydropyridin-3-yl]malonate

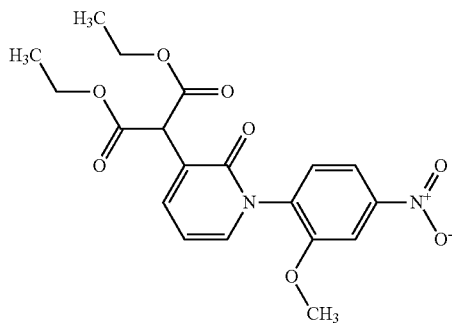 [SMILES: CCOC(=O)C(C(=O)OCC)c1cccn(-c2ccc([N+](=O)[O-])cc2OC)c1=O]

39.3 g of sodium tert-butylate (0.41 mol) were introduced as initial charge in 300 ml of dioxane, and 65.5 g of diethyl malonate (0.41 mol) were added dropwise over the course of 15 min such that the temperature does not exceed 30° C. After 1 h, 2.70 g (8.8 mmol) of bis(2-pyridinecarboxylato)copper (II) complex and 38.0 g (0.12 mol) of 3-bromo-1-(2-methoxy-4-nitrophenyl)pyridin-2(1H)-one were added and the reaction mixture was heated at reflux for 8 h. After cooling to RT, the mixture was further stirred overnight. The reaction mixture was filtered off from the solid with suction, the residue was after-washed with dioxane and the combined organic fractions were evaporated to ca. 300 g on a rotary evaporator. The crude solution was used in the next stage without further purification.

LC-MS (method 4): $R_t$=1.00 min.
MS (ES+): [M+H]$^+$ 405

Example 7

Preparation of [1-(2-methoxy-4-nitrophenyl)-2-oxo-1,2-dihydropyridin-3-yl]acetic acid

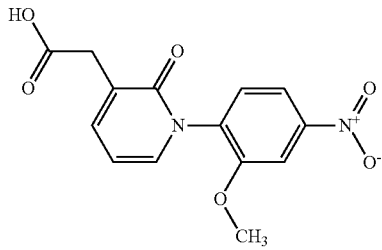 [SMILES: COc1cc([N+](=O)[O-])ccc1-n1cccc(CC(=O)O)c1=O]

The crude product solution of diethyl [1-(2-methoxy-4-nitrophenyl)-2-oxo-1,2-dihydropyridin-3-yl]malonate (maximum 0.12 mol) was diluted with 390 ml of water, and 39 ml of concentrated sodium hydroxide solution were slowly added. The reaction mixture was stirred at 45° C. for 90 min, cooled to RT, diluted with water and extracted three times with dichloromethane. The organic phase was discarded, and the aqueous phase was admixed with 300 ml of dichloromethane and adjusted to pH 1 at 15° C. with concentrated hydrochloric acid. Even in a weakly acidic medium, the evolution of carbon dioxide arises. After warming to RT, stirring was carried out for 1 h, then the phases were separated and the organic phase was dried over sodium sulphate, filtered and concentrated to dryness on a rotary evaporator. The residue was stirred with acetonitrile, filtered with suction, after-washed and dried in vacuo. This gave 17.4 g (49%) of the desired compound. The mother liquor was evaporated to dryness, stirred with acetonitrile and worked-up analogously. This gave a further 3.6 g (10%) of the desired compound.

HPLC (method 2): $R_t$=3.17 min.
LC-MS (method 4): $R_t$=0.69 min.
LC-MS (method 5): $R_t$=0.75 min.
$^1$H NMR (400 MHz, DMSO-$d_6$): δ [ppm]=3.40 (s, 2H), 3.90 (s, 3H), 6.31 (t, 1H), 7.45-7.50 (m, 2H), 7.61 (d, 1H), 7.94 (dd, 1H), 7.98 (m, 1H), 12.21 (br. s, 1H).
MS (ES+): [M+H]$^+$ 305.

Example 8

Preparation of 3-(2-hydroxyethyl)-1-(2-methoxy-4-nitrophenyl)pyridin-2(1H)-one

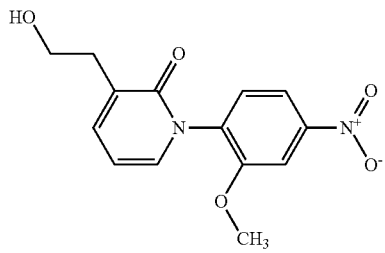 [SMILES: COc1cc([N+](=O)[O-])ccc1-n1cccc(CCO)c1=O]

21.0 g (69.0 mmol) of [1-(2-methoxy-4-nitrophenyl)-2-oxo-1,2-dihydropyridin-3-yl]acetic acid were introduced as initial charge in 210 ml of THF, and 104 ml of 1M borane solution in THF were added dropwise at RT. The temperature increased to 27° C. during this addition. The reaction mixture was stirred overnight at RT. Following dilution with 400 ml of dichloromethane, 400 ml of 1N sodium hydroxide solution were added with cooling and the mixture was stirred for 30 min. The phases were separated, and the organic phase was washed with water, dried over sodium sulphate, filtered and evaporated to dryness on a rotary evaporator. This gave 17.0 g (85%) of crude product which were further reacted without purification.

LC-MS (method 5): $R_t$=0.76 min.
MS (ES+): [M+H]$^+$ 291.

Example 9

Preparation of 2-(bromomethyl)-1-fluoro-4-nitrobenzene

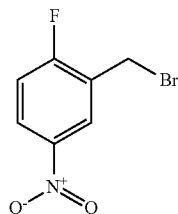 [SMILES: O=[N+]([O-])c1ccc(F)c(CBr)c1]

Benzyl Alcohol/Phosphorus Tribromide Method 70.0 g (0.41 mol) of 2-fluoro-5-nitrobenzyl alcohol were introduced as initial charge in 470 ml of chloroform, and 55.4 g (0.21 mol) of phosphorus tribromide were added. During this addition, the temperature increased to 37° C. The reaction mixture was stirred for min at 60° C. After cooling to RT, the mixture was neutralized (pH=7) by adding saturated aqueous sodium hydrogen carbonate solution. The organic phase was separated off and the aqueous phase was extracted with 50 ml of dichloromethane. The combined organic phases were dried over sodium sulphate, filtered and evaporated to dryness on a rotary evaporator. The solid obtained was dried in vacuo. This gave 93.7 g (98%) of the desired compound, which was reacted further without purification.

N-Bromosuccinimide/Toluene Method 905 g (5.83 mol) of 2-fluoro-5-nitrotoluene and 1038 g (5.83 mol) of N-bromosuccinimide were introduced as initial charge in 5.83 l of chloroform, 47.8 g (0.29 mol) of 2,2'-azobis[isobutyronitrile] were added and the reaction mixture was heated at reflux for 18 h. After cooling to RT, the liquid was filtered off from the solid by suction and the filtrate was divided into three portions. These were absorbed in each case on 1.5 kg of silica gel (0.06-0.2) and chromatographically purified on in each case 10 kg of silica gel with 160 l of ethyl acetate:petroleum ether (2.5:97.5). The product fractions were combined and evaporated to dryness on a rotary evaporator, and the residue was extracted by stirring with petroleum ether for 10 min. The solid was filtered off with suction, after-washed with petroleum ether and dried in vacuo. 385 g (28%) were obtained.

HPLC (method 3): $R_t$=3.95 min.

$^1$H NMR (400 MHz, DMSO-$d_6$): δ [ppm]=4.82 (s, 2H), 7.57 (t, 1H), 8.30 (ddd, 1H), 8.55 (dd, 1H).

MS (EI$^+$): [M-Br]$^+$ 154.

Example 10

Preparation of 1-fluoro-2-(methoxymethyl)-4-nitrobenzene

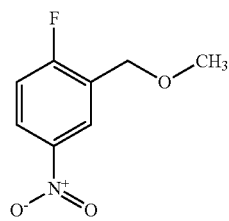

Under argon, 250 g (1.07 mol) of 2-(bromomethyl)-1-fluoro-4-nitrobenzene were introduced as initial charge in 2.5 l of methanol, 371 g (1.60 mol) of silver(I) oxide were added and the mixture was stirred for 2.5 h at 52-56° C. After cooling to RT, suction filtration over kieselguhr was carried out, followed by after-washing with methanol, and the solvent was removed on a rotary evaporator. The crude product was purified by distillation on a short-path evaporator at a jacket temperature of 104° C. and 0.56 mbar. This gave 184.5 g (93%) of the desired product.

HPLC (method 3): $R_t$=3.99 min.

GC-MS (EI) (method 7): $R_t$=4.52 min.

$^1$H NMR (400 MHz, DMSO-$d_6$): δ [ppm]=3.37 (s, 3H), 4.57 (s, 2H), 7.52 (t, 1H), 8.25-8.33 (m, 2H).

MS (EI$^+$): [M]$^+$ 185 (5%), 184 (45%) [M-OMe]$^+$ 154 (90%).

Example 11

Preparation of 3-bromo-1-[2-(methoxymethyl)-4-nitrophenyl]pyridin-2(1H)-one

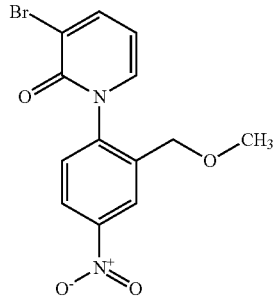 [SMILES: COCc1cc([N+](=O)[O-])ccc1-n1cccc(Br)c1=O]

Under argon, 44.2 g (85% purity, 216 mmol) of 3-bromopyridone in 450 ml of N-methylpyrrolidone were introduced as initial charge, and 29.1 g of potassium tert-butanolate (259 mmol) were added in portions such that the temperature remained below 30° C. The mixture was stirred for 1 h and then 40 g (216 mmol) of 1-fluoro-2-(methoxymethyl)-4-nitrobenzene were added. The reaction mixture was stirred for 4 h at 80° C., cooled to RT and stirred into an ice/water mixture. The pH was adjusted to pH=4 with semiconcentrated hydrochloric acid, the mixture was extracted with ethyl acetate, and the organic phase was dried over sodium sulphate, filtered and evaporated to dryness on a rotary evaporator. The residue was dissolved in 2 l of dichloromethane, absorbed on five times the amount of silica gel and chromatographically purified on silica gel with ethyl acetate:dichloromethane 3:97 and 5:95. The product fractions were evaporated to dryness on a rotary evaporator and the residue was dried in vacuo. This gave 55 g (73%) of the desired product.

HPLC (method 3): $R_t$=3.50 min.

LC-MS (method 6): $R_t$=1.95 min.

$^1$H NMR (400 MHz, DMSO-$d_6$): δ [ppm]=3.26 (s, 3H), 4.27 (d, 1H), 4.34 (d, 1H), 6.35 (t, 1H), 7.69 (dd, 1H), 7.71 (d, 1H), 8.09 (dd, 1H), 8.32 (dd, 1H), 8.37 (d, 1H).

MS (ES+): [M+H]$^+$ 339 or 341.

Example 12

Preparation of diethyl-{1-[2-(methoxymethyl)-4-nitrophenyl]-2-oxo-1,2-dihydropyridin-3-yl}malonate

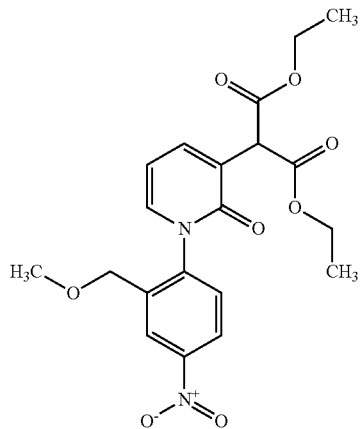 [SMILES: CCOC(=O)C(C(=O)OCC)c1cccn(-c2ccc([N+](=O)[O-])cc2COC)c1=O]

Under argon, a suspension of 49.3 g (513 mmol) of potassium tert-butanolate was introduced as initial charge at RT in 360 ml of dioxane, and 82.2 g (513 mmol) of diethyl malonate were added such that the temperature remained below 30° C. The reaction mixture was stirred for 1 h at RT, 3.4 g (11.0 mmol) of bis(2-pyridinecarboxylato)copper(II) complex and 49.7 g (147 mmol) of 3-bromo-1-[2-(methoxymethyl)-4-nitrophenyl]pyridin-2(1H)-one were added and the mixture was stirred for 4.5 h at 95° C. A further 2.0 g (6.5 mmol) of bis(2-pyridinecarboxylato)copper(II) complex were added and the reaction mixture was stirred overnight at 95° C. After cooling to RT, the mixture was diluted with 0.9 l of ethyl acetate, 1.8 l of 3N hydrochloric acid were added and the mixture was stirred for 15 min at RT. The aqueous phase was extracted with 0.9 l of ethyl acetate and the combined organic phases were washed with saturated aqueous sodium chloride solution. After drying over sodium sulphate, filtration and removal of the solvent on a rotary evaporator, the residue was dried in vacuo. This gave 115 g of crude product, which was reacted further without purification.

HPLC (method 3): $R_t$=3.96 min.
LC-MS (method 4): $R_t$=1.01 min.
$^1$H NMR (400 MHz, DMSO-$d_6$): δ [ppm]=1.18 (t, 3H), 1.20 (t, 3H), 3.24 (s, 3H), 4.11-4.25 (m, 5H), 4.31 (d, 1H), 4.84 (s, 1H), 6.46 (t, 1H), 7.56 (dd, 1H), 7.65 (dd, 1H), 7.67 (d, 1H), 8.30-8.34 (m, 1H), 8.35 (d, 1H).
MS (ES+): [M+H]$^+$ 419.

Example 13

Preparation of {1-[2-(methoxymethyl)-4-nitrophenyl]-2-oxo-1,2-dihydropyridin-3-yl}acetic acid

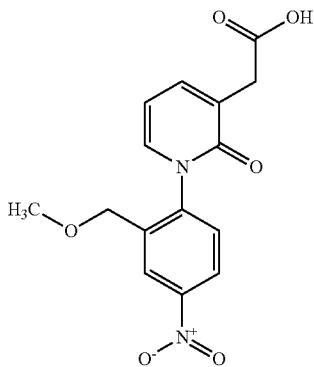 [SMILES: COCc1cc([N+](=O)[O-])ccc1-n1cccc(CC(=O)O)c1=O]

115 g (maximum 147 mmol) of the crude product of diethyl-{1-[2-(methoxymethyl)-4-nitrophenyl]-2-oxo-1,2-dihydropyridin-3-yl}malonate were introduced as initial charge in 470 ml of dioxane at RT, 940 ml of 2N sodium hydroxide solution were added and the reaction mixture was stirred for 1.5 h at RT. By adding 313 ml of concentrated hydrochloric acid, the pH was adjusted to 1 and the mixture was then stirred for 2 h at 50° C. After cooling to RT, extraction was carried out three times with in each case 1.17 l of ethyl acetate. The combined organic phases, were washed three times with in each case 780 ml of saturated aqueous sodium chloride solution, dried over sodium sulphate, filtered and evaporated to dryness on a rotary evaporator. The residue was dissolved in a small amount of dichloromethane and chromatographically purified over 1.96 kg of silica gel (0.04-0.06 mm) with methanol:dichloromethane 5:95 to 1:9. The product fractions were evaporated to dryness on a rotary evaporator. 34.9 g (75% over 2 stages) of the desired product were isolated as oil.

HPLC (method 3): $R_t$=3.16 min.
$^1$H NMR (400 MHz, DMSO-$d_6$): δ [ppm]=3.25 (s, 3H), 3.43 (s, 2H), 4.21 (d, 1H), 4.31 (d, 1H), 6.37 (t, 1H), 7.53 (m, 2H), 7.64 (d, 1H), 8.30 (dd, 1H), 8.34 (m, 1H), 12.27 (br. s, 1H).
MS (ES+): [M+H]$^+$ 319.

Example 14

Preparation of 3-(2-hydroxyethyl)-1-[2-(methoxymethyl)-4-nitrophenyl]pyridin-2(1H)-one

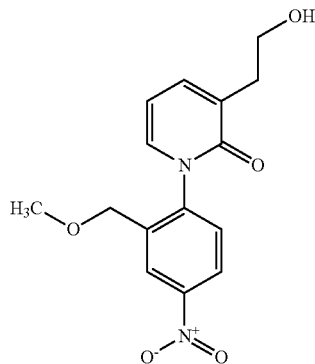 [SMILES: COCc1cc([N+](=O)[O-])ccc1-n1cccc(CCO)c1=O]

Under argon, 37.7 g (109 mmol) of {1-[2-(methoxymethyl)-4-nitrophenyl]-2-oxo-1,2-dihydropyridin-3-yl}acetic acid in 310 ml of tetrahydrofuran were introduced as initial charge at RT, and 53.3 g (327 mmol) of borane-diethylaniline complex were added, at first carefully then, after the considerable foaming has abated, rapidly. The reaction mixture was stirred overnight at RT, diluted with 500 ml of ethyl acetate and admixed with 1N hydrochloric acid (1.55 l), at first carefully (considerable foam formation), then rapidly. The reaction mixture was after-stirred for 30 min, the organic phase was separated off and the aqueous phase was extracted again with 500 ml of ethyl acetate. The combined organic phases were washed twice with in each case 500 ml of 1N hydrochloric acid, washed once with 200 ml of 1N sodium hydroxide solution, dried over sodium sulphate, filtered and evaporated to dryness on a rotary evaporator. The residue was chromatographically purified firstly over 500 g of silica gel (0.04-0.06 mm) with methanol:dichloromethane 5:95 then 1:9 and again over 500 g of silica gel (0.04-0.06 mm) with acetone:dichloromethane 3:7. 14.2 g (43%) of the desired product were obtained here.

HPLC (method 3): $R_t$=3.19 min.

$^1$H NMR (400 MHz, DMSO-$d_6$): δ [ppm]=2.61 (t, 2H), 3.26 (s, 3H), 3.59 (q, 2H), 4.22 (d, 1H), 4.32 (d, 1H), 4.61 (t, 1H), 6.34 (t, 1H), 7.46 (d, 2H), 7.62 (d, 1H), 8.30 (dd, 1H), 8.35 (m, 1H).

MS (DCI, NH$_3$): [M+H]$^+$ 305.

Example 15

Preparation of 3-bromo-1-(2,6-dimethyl-4-nitrophenyl)pyridin-2(1H)-one

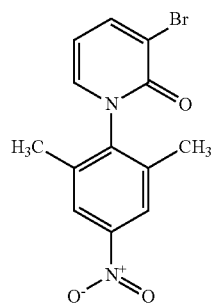 [SMILES: Cc1cc([N+](=O)[O-])cc(C)c1-n1cccc(Br)c1=O]

223 g (38% strength, 0.5 mol) of 2-fluoro-1,3-dimethyl-5-nitrobenzene and 138 g (1.0 mol) of potassium carbonate were introduced as initial charge in 1.95 l of DMSO and heated to 120° C. At this temperature, a solution of 100 g (87% purity, 0.5 mol) of 3-bromopyridone in DMSO was added dropwise. The reaction mixture was stirred for 3.5 h at 120° C., cooled to RT, stirred into water, rendered slightly acidic with hydrochloric acid and extracted with ethyl acetate. The aqueous phase was extracted again with ethyl acetate, and the combined organic phases were washed with water, dried over sodium sulphate, filtered and evaporated to dryness on a rotary evaporator. The crude product was purified over silica gel with dichloromethane then ethyl acetate/dichloromethane=1:20. The isolated product was stirred into diethyl ether/petroleum ether=1:1.5, filtered off with suction and washed with petroleum ether. This gave 75.2 g (47%) of the desired product.

HPLC (method 3): $R_t$=4.17 min.

$^1$H NMR (400 MHz, DMSO-$d_6$): δ [ppm]=2.10 (s, 6H), 6.41 (t, 1H), 7.63 (dd, 1H), 8.14 (dd, 1H), 8.18 (s, 2H).

MS (ES+): [M+H]$^+$ 323 or 325.

Example 16

Preparation of diethyl [1-(2,6-dimethyl-4-nitrophenyl)-2-oxo-1,2-dihydropyridin-3-yl]malonate

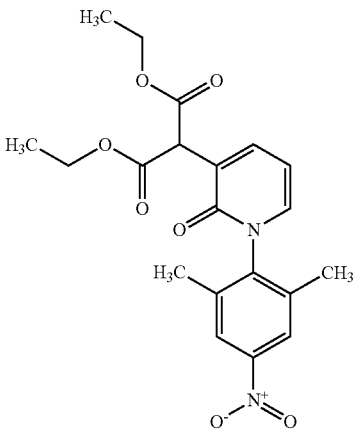 [SMILES: CCOC(=O)C(C(=O)OCC)c1cccn(-c2c(C)cc([N+](=O)[O-])cc2C)c1=O]

Under argon, 42.5 g (379 mmol) of potassium tert-butylate were suspended in 530 ml of dioxane and heated to 55-60° C. At this temperature, a solution of 60.7 g (379 mmol) of diethyl malonate in 100 ml of dioxane was added over 20 min. When the addition was complete, the reaction mixture was stirred for 1 h at 60° C. 6.72 g (21.7 mmol) of bis(2-pyridinecarboxylato)copper(II) complex were then added, as were 35.0 g (108 mmol) of 3-bromo-1-(2,6-dimethyl-4-nitrophenyl)pyridin-2(1H)-one. The reaction mixture was heated at reflux for 8 h and then stirred overnight at RT. Filtering off the liquid from the solid with suction was carried out, followed by after-washing with dioxane, and the filtrate was evaporated to 250 g on a rotary evaporator. The crude solution was further reacted without purification.

LC-MS (method 5): $R_t$=1.18 min.

MS (ES+): [M+H]$^+$ 403.

Example 17

Preparation of [1-(2,6-dimethyl-4-nitrophenyl)-2-oxo-1,2-dihydropyridin-3-yl]acetic acid

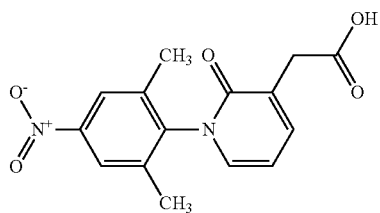 [SMILES: Cc1cc([N+](=O)[O-])cc(C)c1-n1cccc(CC(=O)O)c1=O]

The crude product solution of diethyl [1-(2,6-dimethyl-4-nitrophenyl)-2-oxo-1,2-dihydropyridin-3-yl]malonate in dioxane (maximum 108 mmol) was introduced as initial charge in 350 ml of water, and 35 ml of concentrated sodium hydroxide solution were slowly added. The reaction mixture was stirred for 90 min at 45° C. After cooling to RT, 100 ml of water were added, followed by washing three times with dichloromethane, and the aqueous phase (pH=14) was admixed with 270 ml of dichloromethane. At 10-15° C., 59.5 ml of concentrated hydrochloric acid were slowly added until the pH=1. Even at a weakly acidic pH, carbon dioxide started to evolve. The reaction mixture was warmed to RT and stirred for 1 h, until the gas stopped evolving. Following phase separation, the organic phase was dried over sodium sulphate, filtered and evaporated to dryness on a rotary evaporator. The residue was stirred with 200 ml of methyl tert-butyl ether for 30 min. The crystalline solid was filtered off with suction, washed with methyl tert-butyl ether and dried in vacuo. 14.8 g (47% over 2 stages) of the desired product were obtained. The mother liquor was largely concentrated, the post-precipitation was filtered off with suction, after-washed and dried in vacuo. A further 5.3 g (17% over 2 stages) of the desired product were obtained.

HPLC (method 3): $R_t$=3.39 min.

$^1$H NMR (400 MHz, DMSO-$d_6$): δ [ppm]=2.09 (s, 6H), 3.44 (s, 2H), 6.41 (t, 1H), 7.42 (dd, 1H), 7.54 (dd, 1H), 8.15 (s, 2H), 12.18 (br. s, 1H).

MS (ES+): [M+H]$^+$ 303.

Example 18

Preparation of 1-(2,6-dimethyl-4-nitrophenyl)-3-(2-hydroxyethyl)pyridin-2(1H)-one

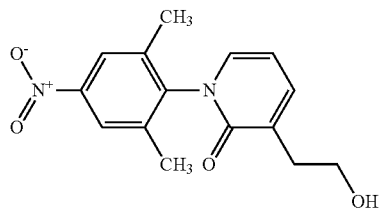 [SMILES: Cc1cc([N+](=O)[O-])cc(C)c1-n1cccc(CCO)c1=O]

26.5 g (87.7 mmol) of [1-(2,6-dimethyl-4-nitrophenyl)-2-oxo-1,2-dihydropyridin-3-yl]acetic acid were introduced as initial charge in 265 ml of THF at RT. 132 ml of 1M borane solution in THF (132 mmol) were added dropwise. During this addition, the temperature increased to 27° C. The reaction mixture was stirred for 1 h at RT and then the same amount of borane solution was added. The reaction mixture was stirred overnight at RT. It was diluted with 500 ml of dichloromethane, and 500 ml of 1N sodium hydroxide solution were added with cooling. The reaction mixture was stirred for 30 min, the phases were separated and the organic phase was washed with water, dried over sodium sulphate, filtered and evaporated to dryness on a rotary evaporator. This gave 12.6 g (48%) of the desired product as crystalline solid.

HPLC (method 3): $R_t$=3.88 min.

$^1$H NMR (400 MHz, DMSO-$d_6$): δ [ppm]=2.09 (s, 6H), 2.63 (t, 2H), 3.58 (q, 2H), 4.61 (t, 1H), 6.37 (t, 1H), 7.35 (dd, 1H), 7.47 (dd, 1H), 8.15 (s, 2H).

MS (ES+): [M+H]$^+$ 291.

The invention claimed is:

1. A process for the preparation of a compound of the formula,

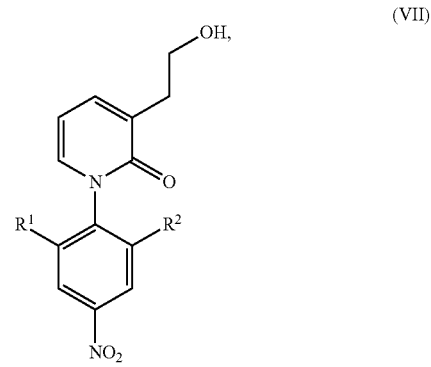

in which $R^1$ is hydrogen or $C_1$-$C_3$-alkyl and $R^2$ is $C_1$-$C_3$-alkyl, or $R^1$ is hydrogen and $R^2$ is $C_1$-$C_3$-alkoxy or $C_1$-$C_3$-alkoxymethyl, comprising reducing the carboxyl group in a compound of the formula

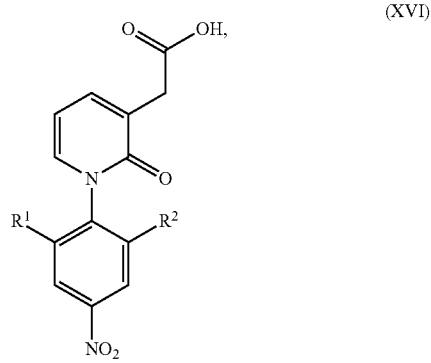

in which $R^1$ and $R^2$ are as defined above, in the presence of a borane complex.

2. The process of claim 1, further comprising preparing the compound of Formula (XVI) by reacting a compound of the formula

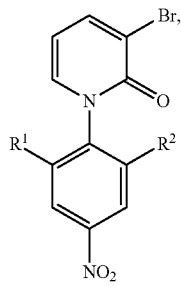

wherein $R^1$ and $R^2$ are defined as in claim 1
in a one-pot process firstly in the presence of a copper catalyst with a malonic acid ester and a base and then with a base and water.

3. The process of claim 1 wherein $R^1$ is methyl and $R^2$ is methyl.

4. The process of claim 1 wherein the borane complex is borane-dimethyl sulphide, borane-tetrahydrofuran, borane diethylaniline or catecholborane.

5. The process of claim 1 wherein the borane complex is used in excess.

6. The process of claim 2, wherein the copper catalyst is provided as a bis(2-pyridinecarboxylato)copper(II) complex or a hydrate thereof, or prepared in-situ from copper iodide, copper chloride, copper(II) bromide, copper(II) triflate or copper(II) sulphate with 2-pyridinecarboxylic acid.

7. The process of claim 6, wherien the copper catalyst is provided as a bis(2-pyridinecarboxylato)copper(II) complex or a hydrate thereof.

8. The process of claim 2 wherein the malonic acid ester is diethylmalonic acid ester, dibenzylmalonic acid ester, di-tert-butylmalonic acid ester or potassium ethylmalonic acid ester.

9. The process of claim 8, wherein the malonic acid ester is diethylmalonic acid ester.

10. The process of claims 2, wherein the base is sodium or potassium tert-butylate, potassium, sodium or caesium carbonate, caesium fluoride or sodium hydride.

11. The process of claim 10, wherein the base is sodium or potassium tert-butylate.

12. A compound of the formula

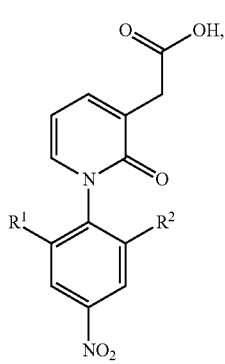

(XVI)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl,
or a salt thereof.

13. The compound of claim 12, wherein $R^1$ is methyl and $R^2$ is methyl.

14. A process for the preparation of a compound of the formula

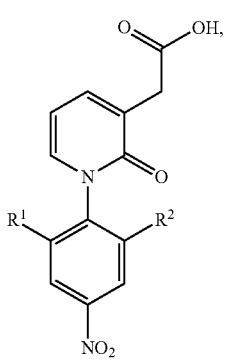

(XVI)

in which
$R^1$ is hydrogen or $C_1$-$C_3$-alkyl
and
$R^2$ is $C_1$-$C_3$-alkyl,
or
$R^1$ is hydrogen
and
$R^2$ is $C_1$-$C_3$-alkoxy or $C_1$-$C_3$-alkoxymethyl,
comprising reacting a compound of the formula

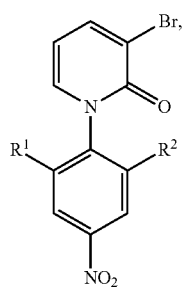

(V)

in which $R^1$ and $R^2$ are as defined above,
is reacted in a one-pot process firstly in the presence of a copper catalyst, wherein the copper catalyst is provided as a bis(2-pyridinecarboxylato)copper(II) complex or a hydrate thereof, with a malonic acid ester and a base and then with a base and water.

15. A process for the preparation of a compound of the formula

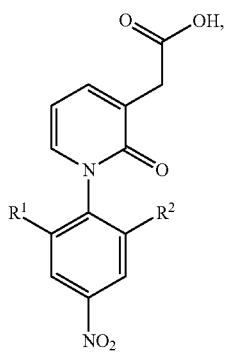

in which
R¹ is hydrogen or $C_1$-$C_3$-alkyl
and
R² is $C_1$-$C_3$-alkyl,
or
R¹ is hydrogen
and
R² is $C_1$-$C_3$-alkoxy or $C_1$-$C_3$-alkoxymethyl, comprising reacting a compound of the formula (XVI)

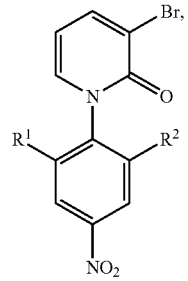

in which R¹ and R² are as defined above,
in a one-pot process firstly in the presence of a copper catalyst with a malonic acid ester and a base and then with a base and water, wherein the base is sodium or potassium tert-butylate.

16. The process of claim 14, wherein R¹ is methyl and R² is methyl.

17. The process of claim 15, wherein R¹ is methyl and R² is methyl.

* * * * *